United States Patent
Chassagne et al.

(10) Patent No.: US 11,384,110 B2
(45) Date of Patent: Jul. 12, 2022

(54) METHOD FOR REMOVING RESIDUAL ORGANIC SOLVENT FROM A CRYSTALLINE OLIGOSACCHARIDE

(71) Applicant: Glycom A/S, Hørsholm (DK)

(72) Inventors: Pierre Chassagne, Beaumont (FR); Martin Matwiejuk, Hamburg (DE); Nikolay Khanzhin, Humlebæk (DK); Markus Jondelius Hederos, Trelleborg (SE)

(73) Assignee: GLYCOM A/S, Hørsholm (DK)

( * ) Notice: Subject to any disclaimer, the term of this patent is extended or adjusted under 35 U.S.C. 154(b) by 0 days.

(21) Appl. No.: 16/346,057

(22) PCT Filed: Oct. 31, 2017

(86) PCT No.: PCT/DK2017/050358
§ 371 (c)(1),
(2) Date: Apr. 29, 2019

(87) PCT Pub. No.: WO2018/077368
PCT Pub. Date: May 3, 2018

(65) Prior Publication Data
US 2019/0248824 A1     Aug. 15, 2019

(30) Foreign Application Priority Data

Oct. 31, 2016   (DK) .......................... PA 2016 70855

(51) Int. Cl.
| | | |
|---|---|---|
| C07H 3/06 | (2006.01) | |
| A61K 31/702 | (2006.01) | |
| F26B 5/04 | (2006.01) | |
| F26B 21/14 | (2006.01) | |
| C07H 13/04 | (2006.01) | |
| C07H 1/00 | (2006.01) | |
| A23L 33/21 | (2016.01) | |
| C07H 1/06 | (2006.01) | |

(52) U.S. Cl.
CPC .............. *C07H 3/06* (2013.01); *A23L 33/21* (2016.08); *A61K 31/702* (2013.01); *C07H 1/00* (2013.01); *C07H 1/06* (2013.01); *C07H 13/04* (2013.01); *F26B 5/04* (2013.01); *F26B 21/14* (2013.01); *A23V 2002/00* (2013.01); *C07B 2200/13* (2013.01)

(58) Field of Classification Search
None
See application file for complete search history.

(56) References Cited

FOREIGN PATENT DOCUMENTS

| | | |
|---|---|---|
| EP | 0900582 A1 | 3/1999 |
| EP | 1405856 A1 | 4/2004 |
| JP | 2004230355 A | 8/2004 |
| WO | 2011100980 A1 | 8/2011 |
| WO | 2011150939 A1 | 12/2011 |
| WO | 2013185780 A1 | 12/2013 |
| WO | 2014009921 A2 | 1/2014 |
| WO | 2014069625 A1 | 5/2014 |
| WO | 2014075680 A1 | 5/2014 |
| WO | 2014086373 A1 | 6/2014 |
| WO | 2015188834 A1 | 12/2015 |
| WO | 2016086947 A1 | 6/2016 |
| WO | 2016095924 A1 | 6/2016 |

OTHER PUBLICATIONS

Yang, P., Lin, C., Zhuang, W., Wen, Q., Zou, F., Zhou, J . . . & Ying, H. (2016). Insight into a direct solid-solid transformation: a potential approach for the removal of residual solvents. CrystEngComm, 18(10), 1699-1704. (Year: 2016).*

Dunn, J. G. (2006). Thermogravimetry. Encyclopedia of Analytical Chemistry: Applications, Theory and Instrumentation. (Year: 2006).*

Chen, X. (2015)."Human Milk Oligosaccharides (HMOS): Structure, Function, and Enzyme-Catalyzed Synthesis," Elsevier Inc. (vol. 72), Advances in Carbohydrate Chemistry and Biochemistry, pp. 113-190. http://dx.doi.org/10.1016/bs.accb.2015.08.002.

Datta, S. et al., "Crystal Structures of Drugs: Advances in Determination, Prediction and Engineering," Nature, 2004, vol. 3, pp. 42-57.

Takamura, T. et al., "Chemical Modification of Lactose. XIII. Synthesis of Lacto-N-tetraose," Chem. Pharm. Bull., 1979, vol. 28(6), pp. 1804-1809.

Urashima, T. et al. (2011) Nutrition and Diet Research Progress: Milk Oligosaccharides. New York: Nova Science Publishers, Inc. 92 pages.

Kuhn, R. et al., "The constitution of lacto-N-neotetraose," Chemische Berichte, 1962, vol. 95, Abstract.

Kuhn, R. et al., "Three acidic pentasaccharides from human milk," Chemische Berichte, 1962, vol. 95, Absract.

* cited by examiner

*Primary Examiner* — Dale R Miller
(74) *Attorney, Agent, or Firm* — Neal, Gerber & Eisenberg LLP

(57) ABSTRACT

The present invention relates to a method of removing residual organic solvent from crystalline oligosaccharides by the use of water vapour as well as the pharmaceutically and nutritionally suitable crystalline oligosaccharides obtained by said method.

18 Claims, 2 Drawing Sheets

METHOD FOR REMOVING RESIDUAL ORGANIC SOLVENT FROM A CRYSTALLINE OLIGOSACCHARIDE

CROSS REFERENCE TO RELATED APPLICATIONS

This application is a national stage entry pursuant to 35 U.S.C. § 371 of International Application No. PCT/DK2017/050358, filed Oct. 31, 2017, which claims priority to Denmark Patent Application No. PA 2016 70855, filed Oct. 31, 2016, the contents of all of which are fully incorporated herein by reference.

FIELD OF THE INVENTION

The present invention relates to a method of removing organic solvent residue from crystalline oligosaccharides, preferably human milk oligosaccharides (HMOs), and crystalline oligosaccharides, preferably crystalline HMOs with low level of organic solvent residue obtainable by the method.

BACKGROUND OF THE INVENTION

Human milk oligosaccharides (HMOs) have become of great interest in the past few years due to their beneficial effects on human postnatal development. To date, the structures of more than 140 HMOs have been determined (see Urashima et al.: *Milk Oligosaccharides*, Nova Biomedical Books, New York, 2011; Chen *Adv. Carbohydr. Chem. Biochem.* 72, 113 (2015)), and considerably more are probably present in human milk.

Low cost ways have been sought for making industrial quantities of as many as possible of the HMOs, so that their uses in nutritional and therapeutic formulations for infants, as well as possibly children and adults, could be discovered, developed and exploited by researchers worldwide. A few HMOs have recently been chemically synthesized, or become available by biotechnological means, in high quantities and high yields. The final step of the technologies is often crystallization or recrystallization of the individual HMOs from aqueous organic solvent, the organic solvent often being an alcohol, usually methanol (see for example WO 2011/100980, WO 2011/150939, WO 2014/009921, WO 2014/075680, WO 2014/086373, WO 2014/069625, WO 2015/188834, WO 2016/086947, WO 2016/095924, EP-A-1405856, Kuhn et al. *Chem. Ber.* 95, 513 and 518 (1962), Takamura et al. *Chem. Pharm. Bull.* 28, 1804 (1980)).

However, the crystalline HMOs having high assay, synthesized according or similar to the above-mentioned methods, may still be contaminated with residues of organic solvents used as the solvent or co-solvent in the crystallization or recrystallization of the HMOs, which cannot be removed by conventional drying, even under vacuum and/or at elevated temperatures. In order to use the HMOs in nutritional formulations for mammals, especially for humans, it is necessary to substantially reduce such residual solvent level.

The recommended acceptable amounts for residual solvents in food ingredients for the safety of the consumers are far less than those in pharmaceuticals. The *Commission Regulation (EU) No 231/2012 of 9 Mar. 2012 laying down specifications for food additives listed in Annexes II and III to Regulation (EC) No 1333/2008 of the European Parliament and of the Council* (http://data.europa.eu/eli/reg/2012/231/oj) specified the purity criteria of food additives with regard to solvent residues (where appropriate). Although the organic solvent residue limit may vary according to the food additives concerned, the limit of e.g. methanol, which is a very common crystallization/recrystallization solvent or co-solvent, is usually below 100 ppm, and never exceeds 1000 ppm. For pharmaceutically active ingredients the same limit is 3000 ppm (see *Impurities: Guideline for Residual Solvents*, The Intentional Council for Harmonisation of Technical Requirements for Pharmaceuticals for Human Use (ICH), http://www.ich.org/products/guidelines/quality/quality-single/article/impurities-guideline-for-residual-solvents.html). Albeit the competent food regulatory authorities may decide or recommend the purity of food ingredients on a case by case basis (including exposure estimates in their consideration), it is very likely that the organic solvent residue limit in an HMO which is to be intended to use in human food does not deviate substantially from that of the food additives. Therefore e.g. the approved level of methanol residue in HMOs can be expected to be around 50-100 ppm.

WO 2013/185780 disclosed a method for removing, or at least reducing substantially, an amount of a residue of an organic solvent in an HMO comprising the step of spray-drying the aqueous solution of the HMO. The method provides an HMO in amorphous form.

Accordingly, it is an object of the present invention to provide a method for removing or reducing substantially the amount and/or concentration of organic solvent residues in and/or on an oligosaccharide, particularly HMO, which provides said oligosaccharide/HMO with very low level of organic solvent residues in crystalline form, which low level of organic solvent residues may be acceptable by food regulatory authorities.

SUMMARY OF THE INVENTION

The present invention provides an efficient method for removing the amount and/or or substantially reducing concentration of organic solvent residues in and/or on a crystalline oligosaccharide. The invention further provides a crystalline oligosaccharide obtainable by the latter method, in particular a crystalline HMO, wherein said oligosaccharide/HMO comprise an amount of organic solvent residues that is acceptable for food products.

Accordingly, the first aspect of this invention relates to a method for removing, or reducing substantially, an amount or concentration of a residue of an organic solvent in or on an crystalline oligosaccharide, said method comprising the step of exposing the crystalline oligosaccharide to water vapour. Preferably, the oligosaccharide is a crystalline hydrate.

The second aspect of the invention relates to a crystalline oligosaccharide hydrate having substantially no, or at least a low amount or concentration of, organic solvent residue. The low amount or concentration of organic solvent residue is preferably not more than 100 ppm, more preferably, between 50-100 ppm or less.

Another aspect of the invention relates to the use of water vapour for removing or reducing substantially an amount or concentration of a residue of an organic solvent in or on an oligosaccharide which is in its crystalline hydrate form.

In one embodiment of any of the aspects above, the oligosaccharide is an HMO.

In one embodiment of the invention, the organic solvent is a lower alcohol, ketone, ester or acid.

Another aspect of the invention relates to crystalline oligosaccharide hydrates comprising an organic solvent residue therein or thereon in an amount of at most 100 ppm obtainable by the method according to the first aspect of the invention.

BRIEF DESCRIPTION OF THE FIGURES

The invention will be described in further details hereinafter with reference to the accompanying figures, in which.

DETAILED DESCRIPTION OF THE INVENTION

Figure 1:
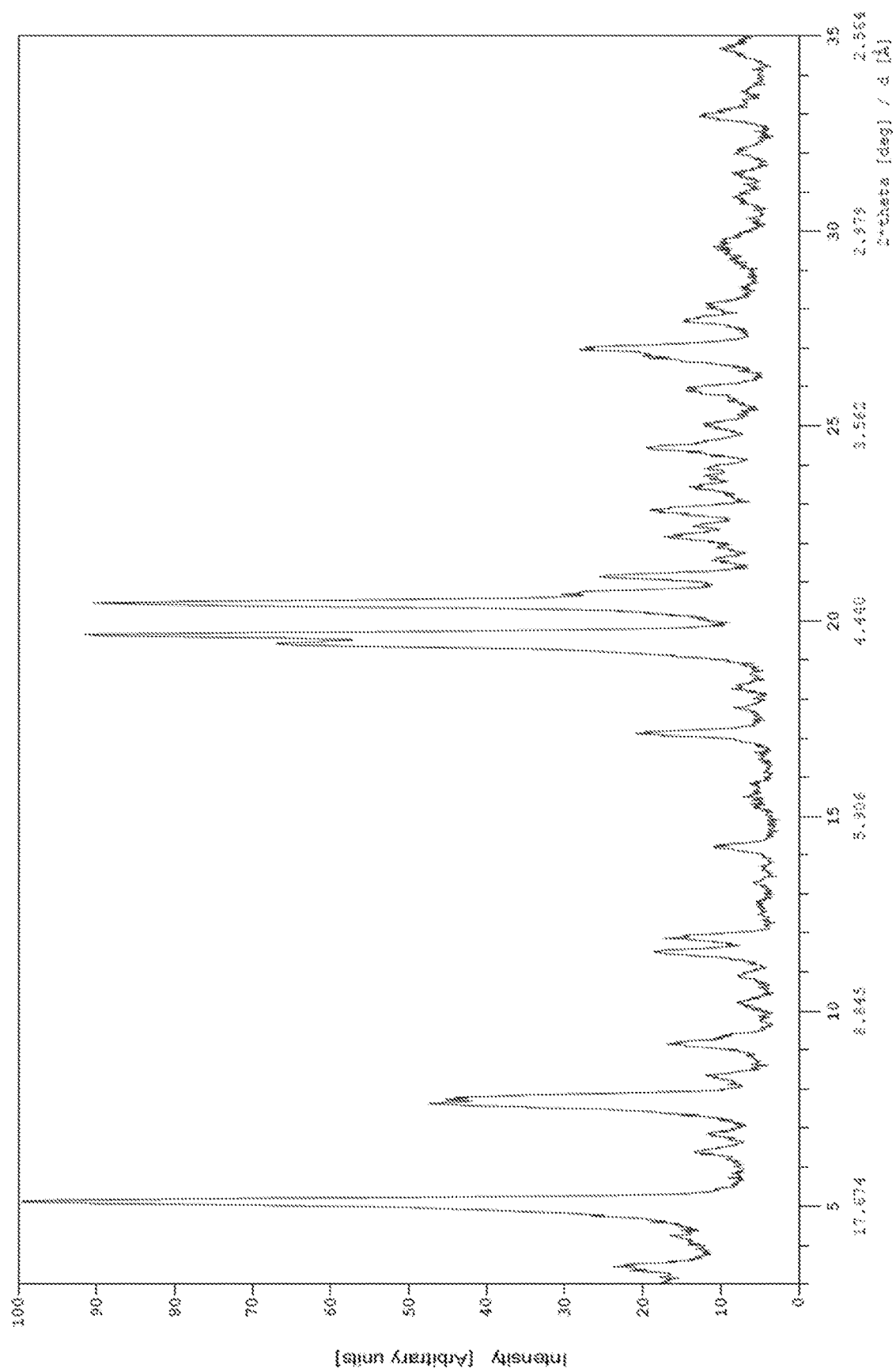
FIG. 1 shows the powder X-ray diffraction pattern of the crystalline pLNnH hydrate prepared according to Example 6.

The term "oligosaccharide" preferably means a sugar polymer having a linear or branched structure containing at least two monosaccharide units that are linked to each other by interglycosidic linkages. The oligosaccharides in the context of the present invention are preferably in free form, i.e. they do not contain a protective group on any of their free anomeric, primary and secondary OH-groups (e.g. an ether, ester, acetal, etc.), and—in aminodeoxy sugars—they do not contain a protective group on their free $NH_2$-groups other than acetyl. The oligosaccharides are preferably di-, tri-, tetra-, penta- or hexasaccharides.

The term "monosaccharide" preferably means a sugar (carbohydrate) of 5-9 carbon atoms that is an aldose (e.g. D-glucose, D-galactose, D-mannose, D-ribose, D-arabinose, L-arabinose, D-xylose, etc.), a ketose (e.g. D-fructose, D-sorbose, D-tagatose, etc.), a deoxysugar (e.g. L-rhamnose, L-fucose, etc.), a deoxy-aminosugar (e.g. N-acetylglucosamine, N-acetylmannosamine, N-acetylgalactosamine, etc.), an uronic acid, an aldonic acid, a ketoaldonic acid (e.g. sialic acid), an aldaric acid or a sugar alcohol.

The term "human milk oligosaccharide" or "HMO" refers to tri-, tetra- and higher oligosaccharides found in human breast milk (Urashima et al.: *Milk Oligosaccharides*, Nova Biomedical Books, New York, 2011; Chen *Adv. Carbohydr. Chem. Biochem.* 72, 113 (2015)). Preferably, an HMO is selected from the group consisting of trisaccharides (such as 2'-FL (2'-O-fucosyllactose), 3-FL (3-O-fucosyllactose), 3'-SL (3'-O-sialyllactose), 6'-SL (6'-O sialyllactose), β'-GL (3'-O-β-galactosyllactose), β4'-GL (4'-O-β-galactosyllactose), β6'-GL (6'-O-β-galactosyllactose) or lacto-N-triose II (GlcNAc(β1-3)Gal(β1-4)Glc)), tetrasaccharides (such as DFL (2',3-di-O-fucosyllactose), SFL (3-O-fucosyl-3'-O-sialyllactose), LNT (lacto-N-tetraose or LNnT (lacto-N-neotetraose)), pentasaccharides (such as LNFP I (lacto-N-fucopentaose I), LNFP II (lacto-N-fucopentaose II), LNFP III (lacto-N-fucopentaose III), LNFP V (lacto-N-fucopentaose V), LST a (sialyllacto-N-tetraose a), LST b (sialyllacto-N-tetraose b) LNH or LST c (sialyllacto-N-tetraose c)) and hexasaccharides (such as LNH (lacto-N-hexaose), LNnH (lacto-N-parahexaose), pLNH (para-lacto-N-hexaose), pLNnH (para-lacto-N-neohexaose), LNFDH I (lacto-N-difucohexaose I), LNFDH II (lacto-N-difucohexaose II), LNFDH III (lacto-N-difucohexaose III), F-LST a (fucosyl-sialyllacto-N-tetraose a), F-LST b (fucosyl-sialyllacto-N-tetraose b), F-LST c (fucosyl-sialyllacto-N-tetraose c) or DS-LNT (disialyllacto-N-tetraose)).

The term "crystalline hydrate of an oligosaccharide" preferably means that the oligosaccharide has, in its crystalline phase, water molecules incorporated into the crystal lattice. Thanks to its small size and ability to participate in multidirectional hydrogen bonding, water may be capable to associate the oligosaccharide molecules to form various regularly arranged 3D structures. On the basis of the location of water in the crystalline structure, crystalline hydrates may be grouped as site hydrates, ion-associates hydrates or channel hydrates; the channel hydrates can be further classified as expanded channel hydrates and planar hydrates (see e.g. Datta et al. *Nat. Rev. Drug. Discov.* 3, 42 (2004)). The amount of crystalline water may be stoichiometric or non-stoichiometric. The degree of hydration can be determined by various means, for example single crystal X-ray diffractometry (SCXRD) or dynamic vapour sorption (DVS), in combination with standard analytical techniques. Powder X-ray diffraction (PXRD) is suitable to characterize crystal forms. In addition, in certain crystalline phases the amount of water participating in the crystalline structure may vary within a certain range without changing its 3D structure, in other words, the same crystalline oligosaccharide can be hydrated in different percentages, as can be evidenced by DVS and PXRD.

The term "lower alcohol" preferably means a low-molecular weight alcohol, that is mono- or dihydroxy alkanes having 1 to 6 carbon atoms, like methanol, ethanol, n-propanol, i-propanol, butanol, hexanol or ethylene glycol, more preferably monohydroxy alkanes, especially a "$C_1$-$C_4$ alcohol", such as methanol, ethanol, isopropanol, n-propanol, n-butanol, sec-butanol and t-butanol.

The term "crystalline oligosaccharides having substantially no organic solvent residue" preferably means that the organic solvent content in or on the crystalline oligosaccharide is below detectable level by gas chromatography, i.e. less than 0.001-0.0001 w/w % or 1-10 ppm.

The above term and definitions are general and applicable to all aspects and embodiments of the invention. Further terms, either general ones or those relevant to particular aspects and embodiments, may be defined below.

It has been observed that certain crystalline oligosaccharides, especially those that are present in the form of their crystalline hydrates, have a strong ability to adsorb organic solvents from which they have been crystallized. Because these organic solvents often have relatively low boiling points and thus they are considered to be volatile, the conventional way to remove them from the crystalline material until reaching a certain required level is usually to apply vacuum and/or elevated temperature. In spite of this the organic solvents may be often retained in the crystals even in a range of around 5000-20000 ppm. This obviously can restrict or even prevent the use of such crystalline oligosaccharide, particularly an HMO, in food and pharmaceutical products. This problem can be overcome by the method of the invention.

It has been surprisingly found, that a modified conventional drying process, which comprises a drying step conducted in a water vapour atmosphere, or a milieu with high humidity, results in an effective solvent residue removal and provides crystalline oligosaccharides having low level organic solvent residue without changing the crystalline phase.

Accordingly, the first aspect of the invention relates to a method for reducing substantially an amount or concentration of a residue of an organic solvent in or on a crystalline oligosaccharide hydrate, comprising the step of exposing the crystalline oligosaccharide hydrate to water vapour.

In the present context, the term "substantial reduction" means that the amount or the concentration of an organic solvent residue in the oligosaccharide crystal after conventional drying, which is above 100 ppm, is lowered to a value which is not more than 100 ppm or below 100 ppm. Preferably, the reduction of an amount or the concentration of an organic solvent residue in the oligosaccharide crystal extents to around 2-3 orders of magnitude, which means that the organic solvent residue content of about 0.5 w/w % or more, like e.g. around 5000-20000 ppm, in the oligosaccharide crystal, which content otherwise cannot be lowered by means of conventional drying, is reduced to a value below 100 ppm, such as below 50 ppm, 25 ppm or 10 ppm. To achieve this, the crystalline oligosaccharide having organic solvent residue to be reduced is, according to the present invention, placed in a milieu wherein the humidity is high. In a preferred embodiment, the crystalline oligosaccharide hydrate is contacted with water vapour in a vessel in which the interior space has, or is maintained at, an elevated humidity relative to that outside of the vessel. The elevated humidity in the interior space of the vessel is advantageously about 60-100% relative humidity (RH %).

Notably, no phase change occurs in the crystalline oligosaccharide hydrates processed upon exposure with water vapour according to the invention, in other words, the PXRD pattern of the substances before and after the exposure do not change. The meaning of wording "exposure with water vapour" is herein interchangeable with "wet drying", "vapour drying" and "vapour stripping".

In one embodiment, substantial reduction of the amount or concentration of an organic solvent residue means that said organic solvent residue is removed from the oligosaccharide crystal so that its amount or concentration drops below detectable level by gas chromatography (less than 0.001-0.0001 w/w % or 1-10 ppm).

The vessel suitable for the purpose of the method can be any laboratory or industrial equipment which is used for drying solid chemical substances such as desiccator, oven, drying column, double cone dryer, conical screw dryer, etc., or any other apparatus which is applicable for drying, e.g. rotavapor. A suitable vessel must not be a closed system, but it should have at least one outlet that is open for water vapour to escape continuously with the traces of the organic solvent removed from the crystalline material. The water vapour may be generated either inside or outside the vessel, in the latter case the water vapour is introduced into the vessel via a suitable tube at a given flowing rate.

In one embodiment, the method is conducted at atmospheric pressure, favourably in a vessel in which water vapour can be generated inside. In order to achieve a high relative humidity quickly and/or accelerate the removal of the organic solvent residue the temperature is advantageously set up above 40° C., such as between 50-60° C., between 60-70° C., or between 70-90° C. This approach provides crystalline oligosaccharides with a very low level of organic solvent residue in a relatively short period, such as hours-to-days range. However, a care shall be taken because the use of high temperatures for a prolonged time may negatively influence the stability of the crystalline oligosaccharide. The suitable temperature range can be determined by a skilled in the art by trial and error, e.g. continuously controlling and analysing the sample during the procedure. If necessary, a lower temperature shall be set, in which case the completion of the solvent residue removal may be longer.

In one preferred embodiment, the method of the present invention is performed under vacuum. Both internal and external water vapour generation can be applied. Under vacuum, lower temperature is necessary to reach the required level of relative humidity, which could be favourable with regard to the product stability. In addition, vacuum creates a stream of vapour that carries out the traces of the organic solvent. A typical temperature range for vacuum stripping is around 40-60° C., or the temperatures at which the crystalline oligosaccharides are stable.

When the water vapour is generated inside the vessel, it is typically done using an open tank, such as a crystallizing dish or a tray, filled with water and placed into the vessel in the same space with the crystalline oligosaccharide. By letting the water evaporate, its vapour saturates the interior space of vessel and the vapour is brought into contact with the crystalline oligosaccharide. The higher the interior temperature, the faster evaporation and quicker removal of the organic solvent take place. However, the temperature cannot exceed the boiling point of the water at the given pressure. It is advisable to set the temperature to at least room temperature.

In case of external vapour generation, the water vapour is typically introduced into the vessel to contact the crystalline oligosaccharide via a tube. In one embodiment, the water vapour is introduced with the aid of a stream of a carrying gas. The carrying gas should be inert, that is it must not react with either water vapour or the crystalline oligosaccharide. Some non-limiting examples of carrying gases are air, nitrogen or argon. Typically, the inert gas is bubbled through water and by the application of positive or negative pressure the stream of the moisturized gas is led into the vessel.

In order to fasten the method of the invention and/or to make it suitable for larger quantities, the method of the invention may, in some embodiments, be preceded by the following steps. The oligosaccharide crystals collected by filtration after crystallization from a solvent system comprising the aqueous organic solvent ("wet cakes") often contain a high amount of the organic solvent (30-50%) and water. The amount of organic solvent can be lowered to around 0.5-2% by implementation of a pre-drying step, which is typically a conventional drying method in a suitable vessel (e.g. using vacuum and/or elevated temperature). The conventional drying in the present context means a mass transfer process consisting of the removal of the organic solvent and water by making them evaporate from the crystalline oligosaccharide, e.g. by heating the wall of the vessel and/or applying vacuum, in a way that both water (humidity) and the organic solvent diffuse/move in the direction of their decreasing concentration, that is from the crystalline solid to the inner space of the vessel, then off the vessel. The wet cakes pre-dried in e.g. an oven may often result in the formation of lumpy crystalline solids that need to be milled and/or sieved to increase the surface of the particles for more efficient contact with the vapour. Particles having a diameter of around 1-2 mm (or less) are usually suitable for the method of the invention.

Accordingly, a certain embodiment of the method comprises the steps of
 a) crystallizing an oligosaccharide hydrate from mixture of water and an appropriate organic solvent,
 b) conventionally pre-drying of the crystals obtained in step a) to remove the majority of organic solvent, and
 c) exposing the crystals obtained in step b) to remove the rest of the organic solvent until its concentration drops to 100 ppm or below.

Furthermore, the method, in some cases, may provide a crystalline material with very low level of organic solvent residue, but supersaturated with vapour of water. In order to meet water content specification of a particular oligosaccharide, an additional drying step may follow the method of the invention, wherein the excess of, or not necessary water is removed by conventional drying (vacuum and/or elevated temperature) in the absence of water vapour and in the presence of a conventional desiccant.

The organic solvent, the residual amount of which is to be removed by the method of the invention, is one of the solvents typically used in oligosaccharide crystallization, mainly as an antisolvent, which is miscible with water fully or partially. Solvents that are frequently suitable include lower alcohols, ketones such as acetone and methyl ethyl ketone, acetic acid, pyridine, methyl sulfoxide, DMF, ethyl acetate or ethers such as diethyl ether, THF, dioxane and mono- or diethyl ethers of ethylene glycol. Preferably, the organic solvent to be removed by the method of the invention is a $C_1$-$C_4$ alkanol, that is methanol, ethanol, isopropanol, n-propanol, n-butanol, sec-butanol or t-butanol, particularly methanol.

To achieve a considerably short stripping time, the crystalline oligosaccharide shall be a hydrate. In this case the kinetics of the residual organic solvent removal is exponential and the oligosaccharide crystal with substantially no, or a very low amount of organic solvent is obtainable within period of a few hours to 1-2 days, depending on the arrangement of the equipment used in the method and/or the bulkiness of the oligosaccharide crystal. Crystalline oligosaccharide anhydrates, however, do not seem to be suitable for the purpose of organic solvent stripping according the method of the invention, because the kinetics of the residual organic solvent removal from those crystalline material is linear of low gradient, therefore the extrapolated time to reach a complete or at least a substantial removal of the organic solvent residue is unpractically long.

In one embodiment, the method of the invention is performed in a drying oven, either at atmospheric pressure or under vacuum. The source of the vapour is a large crystallizing dish or a tray filled with water that is placed at the bottom of the oven. Water is slowly evaporating from the dish over the process time. This particular embodiment is suitable to treat oligosaccharide crystals from gram to kilogram scale.

In another embodiment, the water vapour is led through a fluidized bed of the crystalline oligosaccharide, e.g. using a drying column. This arrangement ensures an improved mass transfer of the vapour to the crystals which increases the stripping efficacy and reduce the time of completion of the process (typically takes less than 24 hours).

In another embodiment, the method of the invention is conducted in a conical screw dryer (suitable for industrial application). The water vapour is let via a jacketed pipe and a sampling valve into the conical dryer at the bottom. The conical dryer is equipped with a rotating mixing screw that mixes the crystalline bulk continuously in an intensive but gentle way, ensuring a good mass transfer of the vapour. The mechanical force of the mixer breaks lumps of the bulk material which incidentally might have formed in the preceding crystallization and/or pre-drying step, therefore a separate milling/sieving step before preforming the method of the invention can advantageously be avoided. Both atmospheric and vacuum stripping is possible in a conical screw dryer.

The crystalline oligosaccharide hydrates, including crystalline HMO hydrates, can be prepared according to the crystallization procedures disclosed in the prior art. For example, 2'-FL (2'-O-fucosyllactose, Fucpα1-2Galpβ1-4Glc) 3/2 hydrate can be crystallized from aqueous methanol, ethanol, propanol or acetone (WO 2014/009921), LNnT (lacto-N-neotetraose, Galpβ1-4GlcNAcpβ1-3Galpβ1-4Glc) polymorph II can be crystallized from aqueous acetone (EP-A-1405856), LNnT polymorph III can be crystallized from aqueous methanol (WO 2011/100980), and DFL (difucosyllactose, Fucpα1-2Galpβ1-4[Fucpα1-3]Glc) hydrate can be crystallized from aqueous ethanol (WO 2016/086947). Other crystalline HMO hydrates are described herein below.

The second aspect of the invention relates to crystalline oligosaccharide hydrates comprising an organic solvent residue therein or thereon which is not more than 100 ppm. The crystalline oligosaccharide of the second aspect is advantageously obtainable by applying the method according to the first aspect of the invention. The organic solvent residue amount or concentration in or on a crystalline oligosaccharide hydrate can be determined by standard methods, e.g. by gas chromatography. Embodiments of the second aspect of the invention includes crystalline oligosaccharide hydrates having an organic solvent residue therein or thereon below a level of 50, 25 or 10 ppm.

In certain embodiments, the crystalline oligosaccharide hydrate comprises organic solvent residue of around 50-100 ppm, 25-75 ppm, 25-50 ppm, 10-50 ppm or 10-25 ppm.

In another embodiment of the second aspect of the invention relates to crystalline oligosaccharide hydrates having substantially no organic solvent residue therein or thereon, that is the amount or concentration of the organic solvent is practically undetectable when determined by standard gas chromatography method (less than around 1-10 ppm).

Exemplary embodiments of crystalline oligosaccharides hydrates are trehalose dihydrate, raffinose pentahydrate and HMO hydrates. Preferred embodiments are HMO hydrates.

More preferably, the crystalline HMO hydrate is selected from the group consisting of 2'-FL polymorph A (3/2 hydrate) characterized in WO 2014/009921, LNnT polymorph II characterized in EP-A-1405856, LNnT polymorph III characterized in WO 2011/100980, DFL hydrate characterized in WO 2016/086947, LNT (lacto-N-tetraose, Galpβ1-3GlcNAcβ1-3Galpβ1-4Glc) hydrate and pLNnH (para-lacto-N-neohexaose, Galpβ1-4GlcNAcβ1-3Galpβ1-4GlcNAcpβ1-3Galpβ1-4Glc) hydrate, even more preferably LNnT polymorph III, DFL hydrate, LNT hydrate and pLNnH hydrate. Preferred embodiments are: LNnT polymorph III comprising ethanol or isopropanol as organic solvent residue which is in not more than 100 ppm; LNnT polymorph III comprising methanol as organic solvent residue which is in not more than 25, preferably 15 ppm; crystalline difucosyllactose hydrate comprising methanol or ethanol as organic solvent residue which is in not more than 100, preferably 50, more preferably 25 ppm; crystalline LNT hydrate comprising methanol or ethanol as organic solvent residue which is in not more than 100, preferably 50, more preferably 25 ppm; crystalline pLNnH hydrate comprising methanol or ethanol as organic solvent residue which is in not more than 100, preferably 50, more preferably 25 ppm.

The crystalline oligosaccharide hydrates having substantially no, or very low level (below 100 ppm) of, organic solvent residue therein or thereon represent a new quality product of crystalline oligosaccharides which have not yet been available by conventional isolation and/or separation means. Notably, although crystalline oligosaccharide crystal have been readily available by crystallizing them from an aqueous organic solvent, the residual amount of that organic solvent proved to be considerably high after drying the crystals under conventional conditions, i.e. high temperature and/or vacuum. The consequence of this drawback is that their commercial use as active substance or ingredient in pharmaceutical and nutritional compositions has been considerably restricted or even practically prevented.

The crystalline oligosaccharide hydrates having substantially no, or very low level (below 100 ppm) of, organic solvent residue therein or thereon according to the second aspect of the invention, and advantageously obtained by the method according to the first aspect of the invention, can be beneficially utilized for making pharmaceutical formulations, nutritional formulations (such as food, drink or feed), food supplements, digestive health functional foods or other consumable products, intended for use with animals, e.g. pets like dogs or cats, or humans, e.g. infants, children, adults or seniors.

Accordingly, the third aspect of the invention relates to a nutritional formulation comprising a crystalline oligosaccharide hydrate having an organic solvent residue therein or thereon below a level of 100 ppm according to the second aspect of the invention.

In a preferred embodiment, the crystalline oligosaccharide hydrate is a crystalline HMO hydrate in the nutritional formulation.

In one embodiment, the nutritional formulation comprising a crystalline oligosaccharide hydrates having an organic solvent residue therein or thereon below a level of 100 ppm can be a food supplement. Such a food supplement may, preferably, contain ingredients as defined for nutritional food above, e.g. vitamins, minerals, trace elements and other micronutrients, etc. The food supplement can be for example in the form of tablets, capsules, pastilles or a liquid. The supplement can contain conventional additives selected from but not limited to binders, coatings, emulsifiers, solubilising agents, encapsulating agents, film forming agents, adsorbents, carriers, fillers, dispersing agents, wetting agents, jellifying agents, gel forming agents, etc.

In another embodiment, the nutritional formulation comprising a crystalline oligosaccharide hydrates having an organic solvent residue therein or thereon below a level of 100 ppm can be digestive health functional food, as the administration of dietetic oligosaccharides, especially an HMO, may provide a beneficial effect on digestive health. Digestive health functional food is, preferably, a processed food used with intention to enhance and preserve digestive health by utilizing the mixture of oligosaccharides according to the present invention as physiologically functional ingredients or components in forms of tablet, capsule, powder, etc. Different terms such as dietary supplement, nutraceutical, designed food, health product can also be used to refer to digestive health functional food.

In another embodiment, the nutritional formulation comprising a crystalline oligosaccharide hydrates according to the second aspect of the invention can be a food, drink or feed that furthermore contains conventional edible micronutrients, vitamins and minerals. The amounts of such ingredients can vary depending on the target group of users, that is whether the consumable product is intended for use with animals, e.g. pets like dogs or cats, or humans, e.g. infants, children, adults, seniors or subjects having specialized needs (e.g., suffering from metabolic disorders). Micronutrients include for example edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolysed cornstarch, etc.) and proteins from casein, soy-bean, whey or skim milk, or hydrolysates of these proteins, but protein from other source (either intact or hydrolysed) can be used as well. Vitamins can be chosen such as vitamin A, B1, B2, B5, B6, 812, C, D, E, H, K, folic acid, inositol and nicotinic acid. The nutritional formulation can contain the following minerals and trace elements: Ca, P, K, Na, CI, Mg, Mn, Fe, Cu, Zn, Se, Cr or I. Furthermore, additional probiotics can be added, e.g. lacto bacteria, *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet can also be further added.

The nutritional formulations as above can be prepared in any conventional manner. For example, it can be prepared by admixing micronutrient components in appropriate proportions. Then the vitamins and minerals are added, but to avoid thermal degradation or decomposition heat sensitive vitamins can be added after homogenization. Lipophilic vitamins can be dissolved in the fat source before mixing. A liquid mixture is formed using water, whose temperature is preferably about between 50-80° C. to help dissolution or dispersal of the ingredients. The crystalline oligosaccharide crystal according to the second aspect can be added at this stage. The resulting mixture is then homogenized by flash heating to about 80-150° C. by means of steam injection, heat exchanger or autoclave. This thermal treatment reduces significantly the bacterial loads as well. The hot mixture is then cooled rapidly to about 60-80° C. If needed, further homogenization can be carried out at this temperature under high pressure of about 2-30 MPa. After cooling heat sensitive constituents can be added at this stage, and the pH and the content of the solids are conveniently adjusted. The resulting mixture is then dried by conventional method such as spray drying or freeze drying to powder. Probiotics can be added at this point by dry-mixing.

The fourth aspect of the invention relates to a pharmaceutical formulation comprising a crystalline oligosaccharide hydrate having an organic solvent residue therein or thereon below a level of 100 ppm according to the second aspect of the invention.

In a preferred embodiment, the crystalline oligosaccharide hydrate is a crystalline HMO hydrate in the pharmaceutical composition.

In one embodiment, the pharmaceutical composition is intended for treating humans, e.g. infants, children, adults and/or seniors and particularly subjects having specialized needs (e.g. those suffering from metabolic or mental disorders, infections, cardio-vascular diseases, etc.). The crystalline oligosaccharide crystal according to the second aspect can be added to a pharmaceutically acceptable carriers such as conventional additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.), to make the pharmaceutical composition. Suitable carriers are described in the most recent edition of Remington's Pharmaceutical Sciences, a standard reference text in the field. When the crystalline oligosaccharide hydrate according to the second aspect is added to the pharmaceutically acceptable carriers, a dosage in the form of for example, but not limited to tablets, powders, granules, suspensions, emulsions, infusions, capsules, injections, liquids, elixirs, extracts and tincture can be made or as other forms, e.g. in a particular formula that is suitable for particular application method, patient group or disease. To the above formulas, if needed, probiotics, e.g. lacto bacteria, *Bifidobacterium* species, prebiotics such as fructooligosaccharides and galactooligosaccharides, proteins from casein, soy-bean, whey or skim milk, carbohydrates, such as lactose, saccharose, maltodextrin, starch or mixtures thereof, lipids (e.g. palm olein, sunflower oil, safflower oil) and/or vitamins and minerals essential in a daily diet can also be further added.

Pharmaceutical compositions of the fourth aspect of the invention can be manufactured by means of any usual manner known in the art, e.g. described in the most recent edition of Remington's Pharmaceutical Sciences, a standard reference text in the field.

The fifth aspect of the invention relates to the use of water vapour in reducing substantially an amount or concentration of a residue of an organic solvent in or on a crystalline oligosaccharide hydrate, preferably in or on a crystalline HMO hydrate. Utilization of water vapour surprisingly lowers the amount or concentration of organic solvent residue left in the crystalline bulk of an oligosaccharide hydrate which cannot be eliminated by conventional drying process, when the water vapour is brought into contact with the crystalline oligosaccharide hydrate containing organic solvent residue. Advantageously, the contact occurs in a vessel in which the concentration of the water vapour is higher than that outside the vessel. This particular use of water vapour provides then crystalline oligosaccharide hydrates of improved quality meaning that they have a very low amount or concentration of organic solvent residue, that is below 100 ppm, such as below 50 ppm, 25 ppm or 10 ppm, therefore are suitable for using them in making pharmaceutical or nutritional composition intended for human consumption.

The sixth aspect of the invention relates to crystalline oligosaccharide hydrates comprising an organic solvent residue therein or thereon in 10-100 ppm or below obtainable by the method according to the first aspect of the invention. The organic solvent residue amount or concentration in or on a crystalline oligosaccharide hydrate can be determined by standard methods, e.g. by gas chromatography. Embodiments of the crystalline oligosaccharide hydrates obtainable by the method according to the first aspect of the invention includes those comprising an organic solvent residue therein or thereon below a level of 50, 25 or 10 ppm, such as of around 50-100 ppm, 25-75 ppm, 25-50 ppm, 10-50 ppm or 10-25 ppm.

Preferred embodiments of the sixth aspect of the invention are HMO hydrates, more preferably the crystalline HMO hydrate is selected from the group consisting of 2'-FL polymorph A (3/2 hydrate), LNnT polymorph II, LNnT polymorph III, DFL hydrate, LNT hydrate and pLNnH hydrate, even more preferably LNnT polymorph III, DFL hydrate, LNT hydrate and pLNnH hydrate. Preferred embodiments are: LNnT polymorph III comprising ethanol or isopropanol as organic solvent residue which is in not more than 100 ppm; LNnT polymorph III comprising methanol as organic solvent residue which is in not more than 25, preferably 15 ppm; crystalline difucosyllactose hydrate comprising methanol or ethanol as organic solvent residue which is in not more than 100, preferably 50, more preferably 25 ppm; crystalline LNT hydrate comprising methanol or ethanol as organic solvent residue which is in not more than 100, preferably 50, more preferably 25 ppm; crystalline pLNnH hydrate comprising methanol or ethanol as organic solvent residue which is in not more than 100, preferably 50, more preferably 25 ppm.

EXAMPLES

Example 1

LNnT polymorph III, crystallized from aqueous methanol (see WO 2011/100980), may contain water from 2.0 to 9.3 w/w % having identical powder X-ray diffractograms.

The wet cake of the crystalline LNnT was pre-dried in a rotavapor at 60° C. and 30 mbar for 2.5 hours. GC analysis of the sample showed a methanol content of 18240 ppm. The pre-dried material was then placed in a drying oven together with a dish containing water, and the temperature was set to 90° C. After 24 and 60 tours of drying the residual methanol was stripped to 15 and 5 ppm, respectively.

Example 2

LNnT polymorph III was crystallized according to WO 2011/100980 from aqueous isopropanol. The wet crystal was dried in a vacuum oven (60° C., 50 mbar) for 24 hours and its residual isopropanol content was 2.19%. The crystals were then milled and further dried in an oven at 90° C. and at atmospheric pressure in the presence of a dish containing water for 20 hours. Then the temperature was lowered to 60° C., the dish containing water was removed and vacuum (50 mbar) was applied ensuring a constant humid interior atmosphere by the inlet of air bubbled through water at room temperature. After 17 hours the isopropanol content was dropped to 94 ppm.

Example 3

LNnT polymorph III was crystallized according to WO 2011/100980 from aqueous methanol. The wet crystal was dried in a vacuum oven (60° C., 50 mbar) and its residual methanol content was 15804 ppm. After milling a sieving (2 mm), the crystals were placed in a drying column, to the bottom of which a tank filled with water was attached via a plastic tube. The top of the column was attached to a vacuum pump. Both the water tank and the drying column filled up with crystalline LNnT polymorph III were kept at 25° C. The water vapour generated by vacuum (17-20 mbar) passed through the bed of LNnT crystals. After given times samples were taken from the fluid bed and their methanol contents were determined by GC:

| time | 0 | 1 h 15 m | 2 h 45 m | 4 h 5 m |
|---|---|---|---|---|
| MeOH (ppm) | 15804 | 737 | 19 | 16 |

Example 4

In the same design of experiment as in Example 3, the temperature of the drying column was kept at 50° C., and the water tank was warmed to 40-45° C. The vacuum was set first at 100 mbar, then 60 mbar. The following values were measured from the LNnT polymorph III samples taken:

| time | 0 | 1 h 10 m | 2 h 30 m |
|---|---|---|---|
| MeOH (ppm) | 15804 | 602 | 13 |
| vacuum (mbar) | — | 100 | 60 |

Example 5

DFL was crystallized according to WO 2016/086947 from aqueous ethanol. The wet crystalline material was dried in a vacuum oven (8 mbar) at 60° C. for 11 hours and at 40° C. for 13 hours. Its residual ethanol content was 1.03%. The drying was continued in the same vacuum oven (30 mbar, 50° C.) but in the presence of a dish containing water. After given times samples were taken and their ethanol contents were determined by GC:

| time | 0 | 15 h | 23 h | 38 h |
|---|---|---|---|---|
| EtOH (ppm) | 10284 | 117 | 49 | 17 |

Example 6

A clear solution of pLNnH in water (BRIX 14.2) was concentrated to a suspension at 70° C. under vacuum (60 mbar) by evaporating the $\frac{5}{6}^{th}$ parts of the water. The suspension was allowed to cool to room temperature while stirred overnight. The solid was filtered, washed with methanol/water (1:1), methanol/water (2:1) and methanol, then dried in a vacuum oven for 27 hours (60° C., 5 mbar). The analysis of the sample showed that the obtained solid was crystalline (see FIG. 1), contained 7.9% water (determined by Karl-Fisher titration) and 870 ppm of methanol (determined by GC). The crystalline solid was further dried in a vacuum oven in the presence of a dish containing water for 3 days (50° C., 30 mbar). The methanol content of the obtained crystals dropped below detectable level by GC (less than 1 ppm).

Example 7

Figure 2:
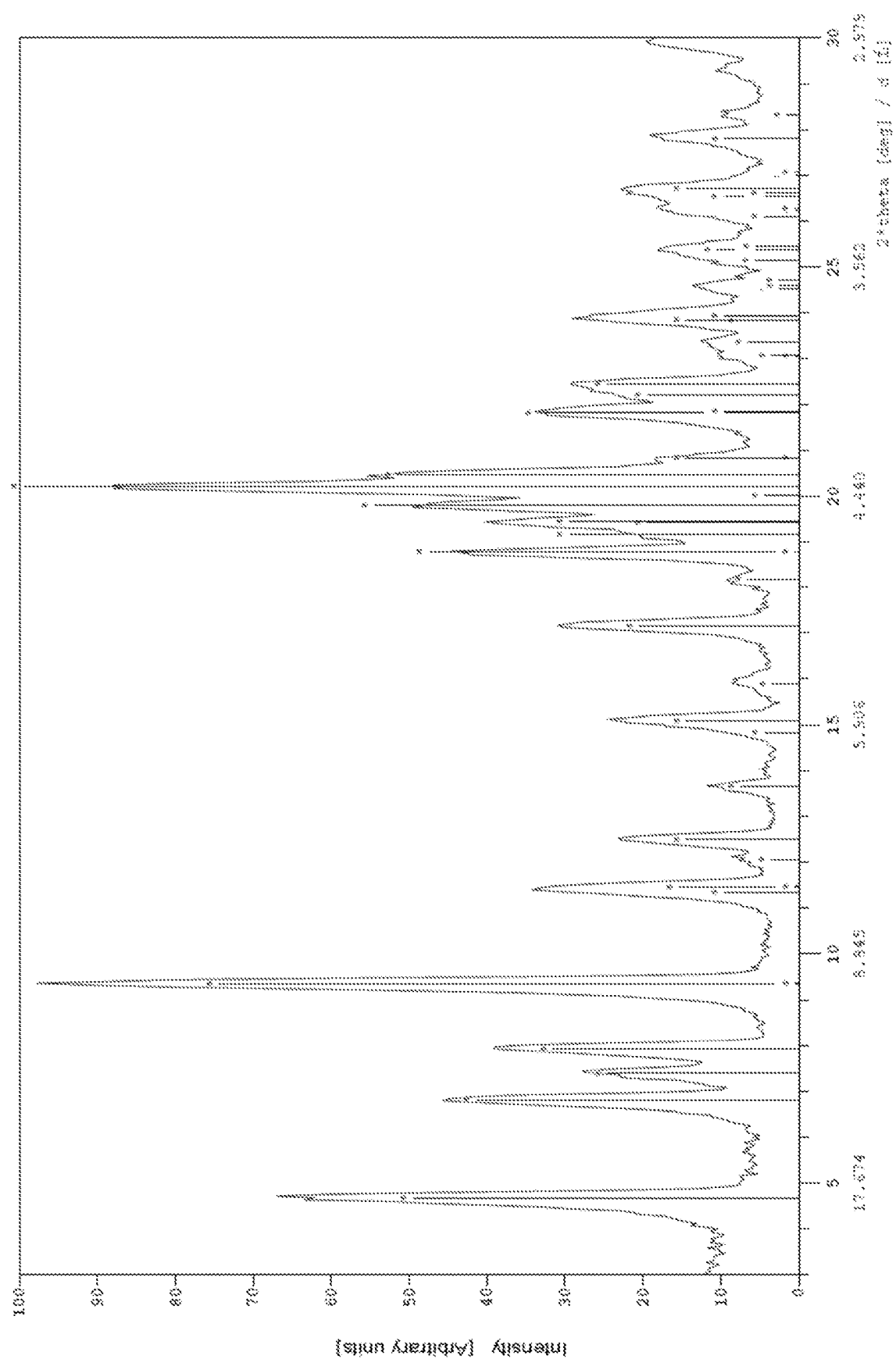
FIG. 2 shows the powder X-ray diffraction patter of the crystalline LNT hydrate prepared according to Example 7.

A) LNT (9.7 g) dissolved in water (33 ml)) was heated to 60° C. Methanol (66 ml) was slowly added over 35 min. The solution was stirred at 60° C. and after 15 min spontaneous nucleation occurred. The suspension was stirred for 2 hours at 60° C. before being slowly cooled to 40° C. over 1.5 hours. The suspension was further stirred at 40° C. for 14 hours. The suspension was then allowed to cool to 25° C. and further stirred at this temperature for 2 hours. Crystals were filtered off and washed with 10 ml of methanol. Wet crystals were dried at 50° C. for at 50 mbar for 21 hours, giving a crystalline material (for PXRD pattern see FIG. 2), having a water content of 9.4% (by Karl-Fisher titration).

B) An aqueous solution containing LNT (34 g) was concentrated to brix 24° C. At 35° C. a first portion of MeOH (150 ml) was added. The solution was seeded. Further MeOH (150 ml) was added in 25 ml portions over a period of 1 hour. The suspension was stirred at 35° C. for 3 hours, then heated up to 55° C., stirred at 55° C. for 6 hours, then cooled down to 35° C. and stirred at 35° C. for 4 hours. The solid was filtered off, washed with 60 ml of MeOH and dried in vacuum oven at 60° C. and 50 mbar for 5 hours to afford a crystalline material (29 g), which was identical, according to PXRD, with the sample obtained above, and had a water content of 9.1% (by Karl-Fisher titration) and a methanol content of 5234 ppm (by GC). This solid was further dried at 70° C. and atmospheric pressure next to a dish of water in the oven for 65 hours, to give 29 g of crystals, the methanol content of which dropped below 10 ppm (by GC).

The invention claimed is:

1. A method for reducing an amount or concentration of a residue of an organic solvent on a crystalline form of a human milk oligosaccharide hydrate, comprising the steps of:
    exposing the crystalline form of a human milk oligosaccharide hydrate to water vapour in a vessel, wherein the interior space of the vessel has, or is maintained at, an elevated humidity relative to that outside the vessel; and
    obtaining the same crystalline form of the oligosaccharide hydrate with reduced amount or concentration of a residue of an organic solvent,
    wherein the organic solvent is selected from the group consisting of a lower alcohol, a ketone, and acetic acid.

2. The method according to claim 1, wherein the elevated humidity in the interior space of the vessel is or is maintained within the range of 60-100 RH %.

3. The method according to claim 1, wherein the amount or concentration of a residue of an organic solvent on the crystalline oligosaccharide hydrate after exposure is less than or equal to 100 ppm.

4. The method according to claim 1, wherein the method is performed under vacuum.

5. The method according to claim 1, wherein the crystalline oligosaccharide hydrate is DFL hydrate.

6. The method according to claim 1, wherein the crystalline human milk oligosaccharide hydrate is LNnT polymorph III.

7. The method according to claim 1, wherein the crystalline human milk oligosaccharide hydrate is LNT hydrate.

8. The method according to claim 1, wherein the crystalline oligosaccharide hydrate is pLNnH hydrate.

9. The method according to claim 1, wherein the lower alcohol is a $C_1$-$C_4$ alkanol.

10. The method according to claim 9, wherein the $C_1$-$C_4$ alkanol is methanol.

11. A nutritional formulation comprising a crystalline human milk oligosaccharide hydrate obtained according to the method of claim 5.

12. A nutritional formulation comprising a crystalline human milk oligosaccharide hydrate obtained according to the method of claim 6.

13. A nutritional formulation comprising a crystalline human milk oligosaccharide hydrate obtained according to the method of claim 7.

14. A nutritional formulation comprising a crystalline human milk oligosaccharide hydrate obtained according to the method of claim 8.

15. A pharmaceutical formulation comprising a crystalline human milk oligosaccharide hydrate obtained according to the method of claim 1.

16. A crystalline human milk oligosaccharide hydrate comprising an organic solvent on the crystalline oligosaccharide hydrate, wherein the amount of the organic solvent on the crystalline oligosaccharide hydrate is less than or equal to 100 ppm, and wherein the crystalline human milk oligosaccharide hydrate is selected from the group consisting of DFL hydrate, LNT hydrate and pLNnH hydrate.

17. A nutritional formulation comprising a crystalline oligosaccharide hydrate according to claim 16.

18. A pharmaceutical formulation comprising a crystalline oligosaccharide-hydrate according to claim 16.

* * * * *